United States Patent
Dasbach et al.

(10) Patent No.: US 12,390,602 B2
(45) Date of Patent: Aug. 19, 2025

(54) APPARATUS FOR REMOVING A NEEDLE SHIELD

(71) Applicant: Sanofi, Paris (FR)

(72) Inventors: Uwe Dasbach, Frankfurt am Main (DE); Thomas Mark Kemp, Herts (GB); William Timmis, Herts (GB); Sarah Bielby, Herts (GB)

(73) Assignee: Sanofi, Paris (FR)

( * ) Notice: Subject to any disclaimer, the term of this patent is extended or adjusted under 35 U.S.C. 154(b) by 925 days.

(21) Appl. No.: 17/616,367

(22) PCT Filed: Jun. 3, 2020

(86) PCT No.: PCT/EP2020/065364
§ 371 (c)(1),
(2) Date: Dec. 3, 2021

(87) PCT Pub. No.: WO2020/245206
PCT Pub. Date: Dec. 10, 2020

(65) Prior Publication Data
US 2022/0323689 A1    Oct. 13, 2022

(30) Foreign Application Priority Data

Jun. 4, 2019 (EP) .................................. 19305718

(51) Int. Cl.
*A61M 5/32* (2006.01)
*A61M 5/20* (2006.01)
*A61M 5/31* (2006.01)

(52) U.S. Cl.
CPC ............ *A61M 5/3204* (2013.01); *A61M 5/20* (2013.01); *A61M 2005/312* (2013.01)

(58) Field of Classification Search
CPC .................. A61M 5/3204; A61M 5/20; A61M 2005/312; A61M 2005/3109; A61M 2205/58

See application file for complete search history.

(56) References Cited

U.S. PATENT DOCUMENTS

2010/0268169 A1* 10/2010 Llewellyn-Hyde .......................
A61M 5/5086
604/192
2012/0323186 A1   12/2012 Karlsen et al.
(Continued)

FOREIGN PATENT DOCUMENTS

| CN | 104968384 A | 10/2015 |
| CN | 108495676 A | 9/2018 |

(Continued)

OTHER PUBLICATIONS

International Preliminary Report on Patentability in International Application No. PCT/EP2020/065364, dated Dec. 7, 2021, 9 pages.
(Continued)

*Primary Examiner* — Tasnim Mehjabin Ahmed
(74) *Attorney, Agent, or Firm* — Fish & Richardson P.C.

(57) ABSTRACT

The disclosure refers to an apparatus, including a needle unit including a needle arranged along a first axis, a needle shield which covers the needle, a main part, a connector for connecting the needle shield to the main part by a positive connection or an adhesive bond, such that the needle shield is removed when the main part is moved along the first axis away from the needle.

14 Claims, 14 Drawing Sheets

(56) References Cited

U.S. PATENT DOCUMENTS

| | | |
|---|---|---|
| 2014/0243753 A1 | 8/2014 | Bostrom |
| 2014/0343503 A1 | 11/2014 | Holmqvist |
| 2015/0367082 A1 | 12/2015 | Ward et al. |
| 2016/0144135 A1 | 5/2016 | Taal et al. |
| 2016/0175539 A1 | 6/2016 | Riedel et al. |
| 2016/0296713 A1* | 10/2016 | Schader ............. A61M 5/3245 |
| 2016/0354551 A1 | 12/2016 | Keim et al. |
| 2017/0361030 A1* | 12/2017 | Moore .................. A61M 5/326 |
| 2018/0272075 A1 | 9/2018 | Stefanov et al. |
| 2018/0344944 A1 | 12/2018 | Wendland et al. |

FOREIGN PATENT DOCUMENTS

| | | |
|---|---|---|
| EP | 2361648 | 8/2011 |
| EP | 2878321 | 6/2015 |
| EP | 3257536 | 12/2017 |
| EP | 3332822 A1 | 6/2018 |
| JP | 2014-530083 A | 11/2014 |
| JP | 2016-526996 A | 9/2016 |
| JP | 2016-538058 A | 12/2016 |
| JP | 2017-500916 A | 1/2017 |
| JP | 2018-535043 A | 11/2018 |
| WO | WO 2013/058697 | 4/2013 |
| WO | WO 2015/007857 | 1/2015 |
| WO | WO 2017/089273 | 6/2017 |
| WO | WO 2017/089274 A1 | 6/2017 |
| WO | WO 2020/039009 | 2/2020 |

OTHER PUBLICATIONS

International Search Report and Written Opinion in International Application No. PCT/EP2020/065364, dated Jul. 31, 2020, 12 pages.

* cited by examiner

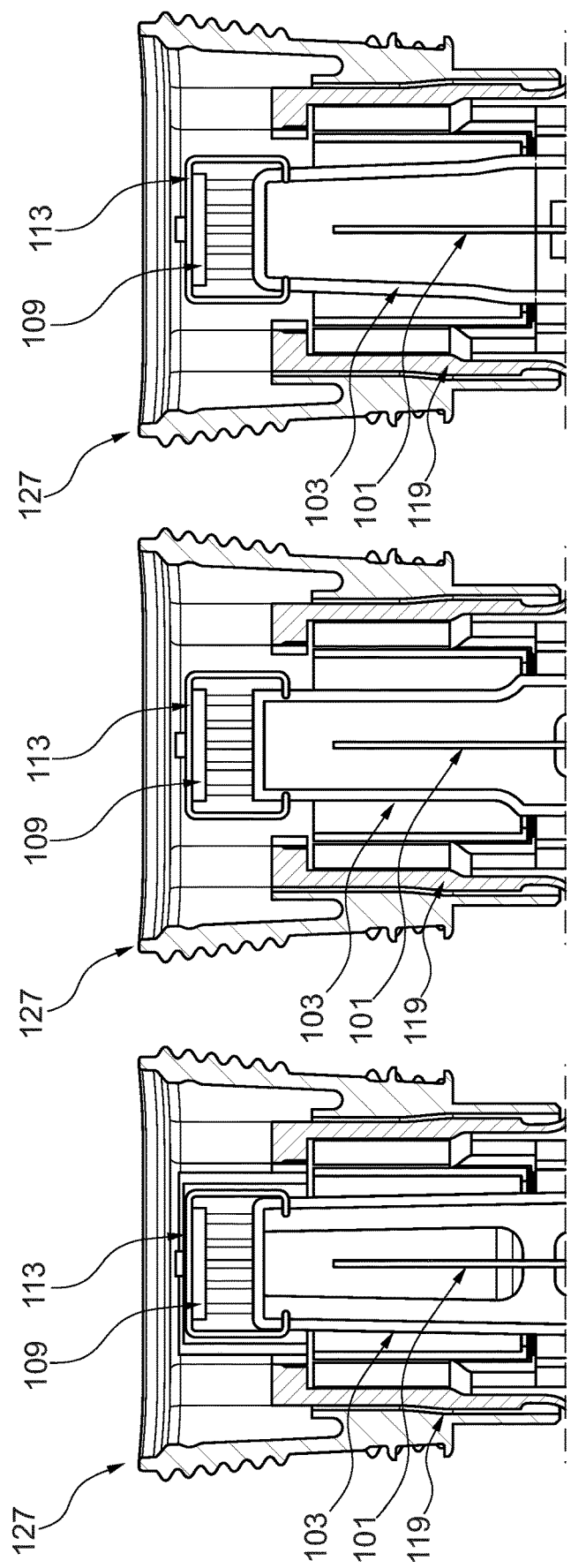

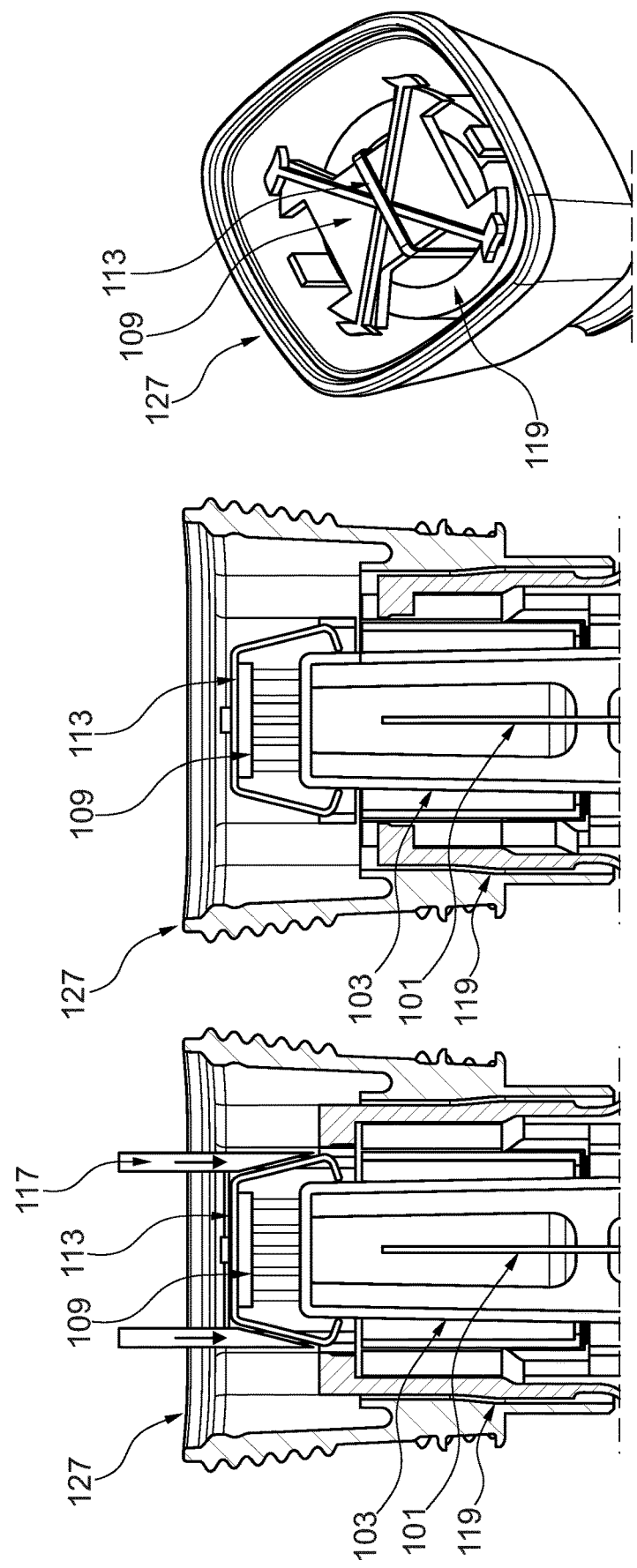

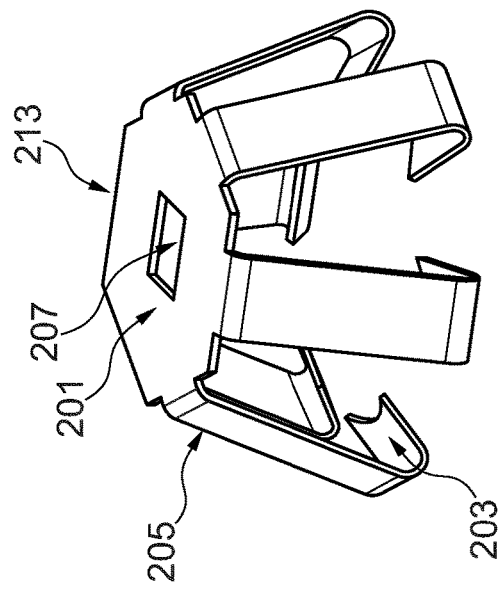
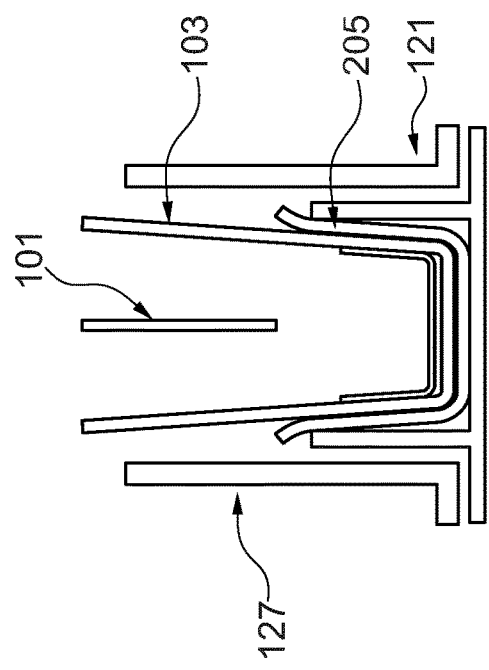
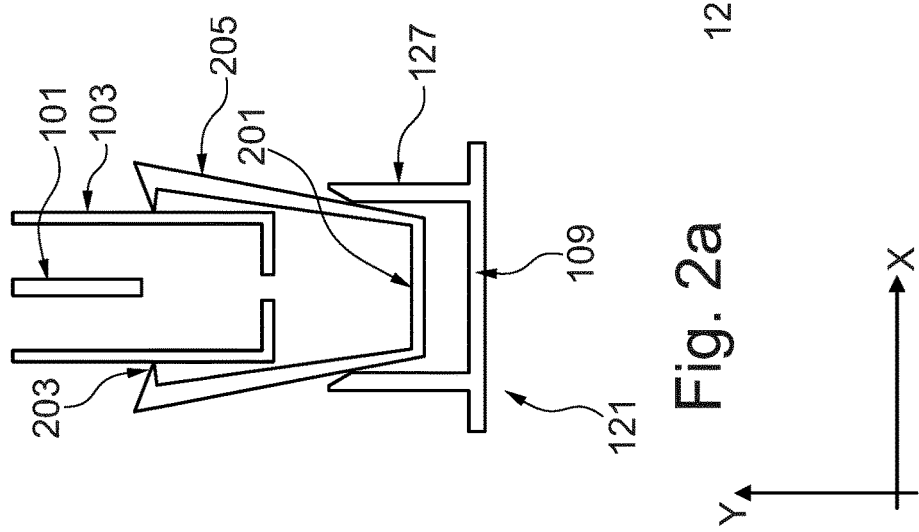

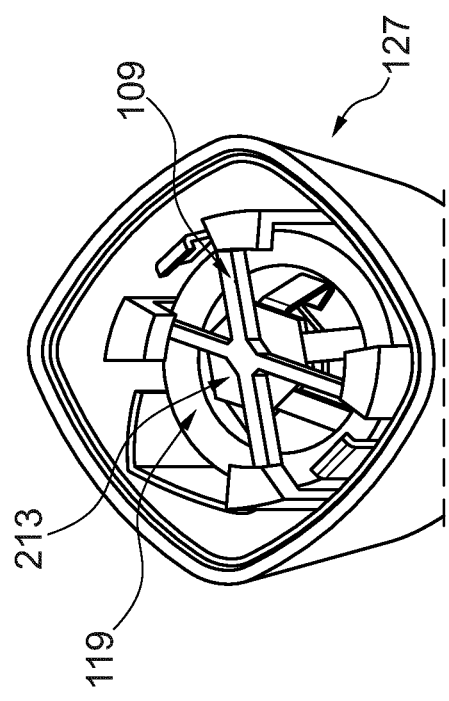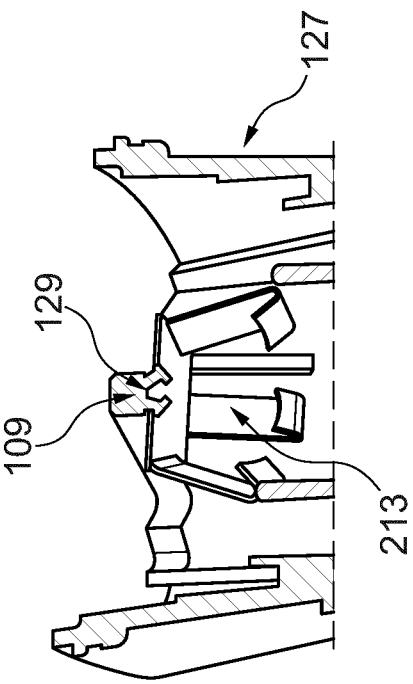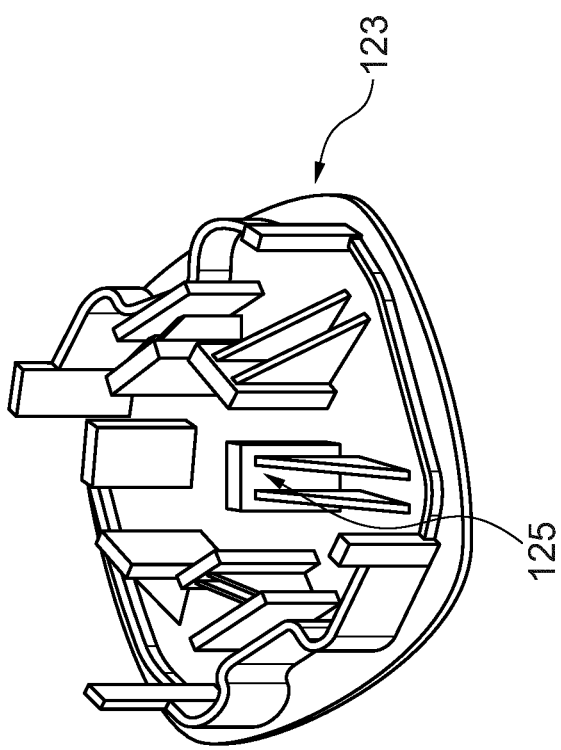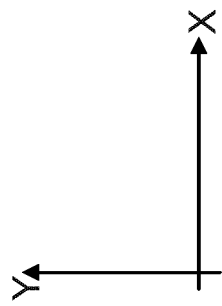

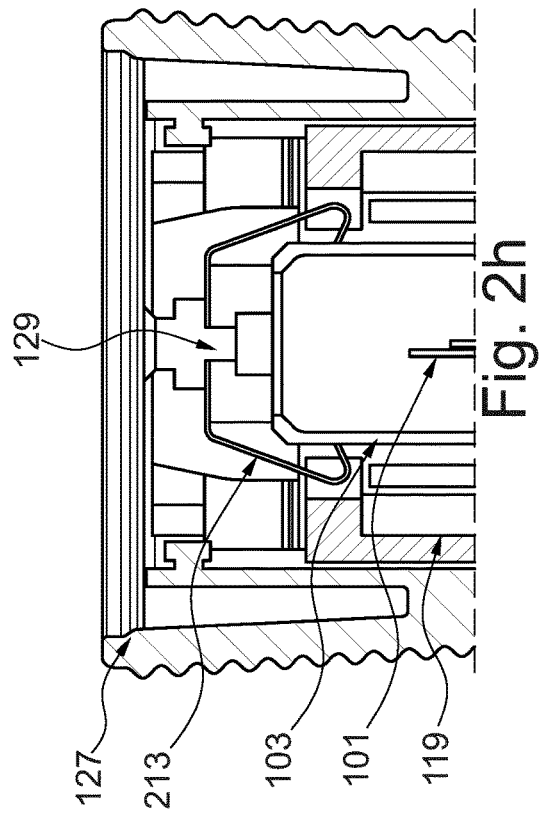
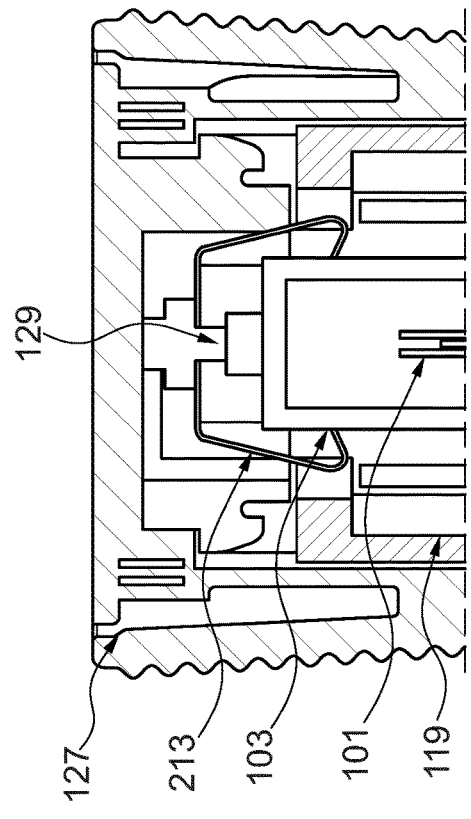
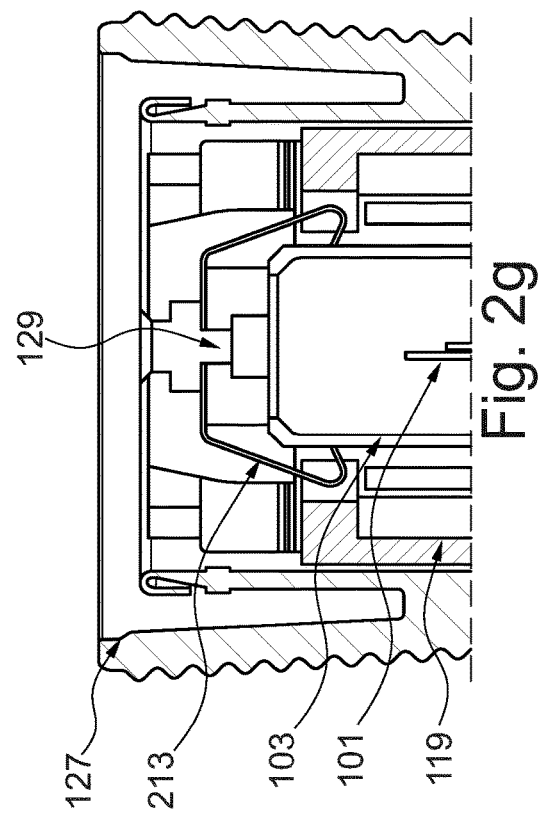
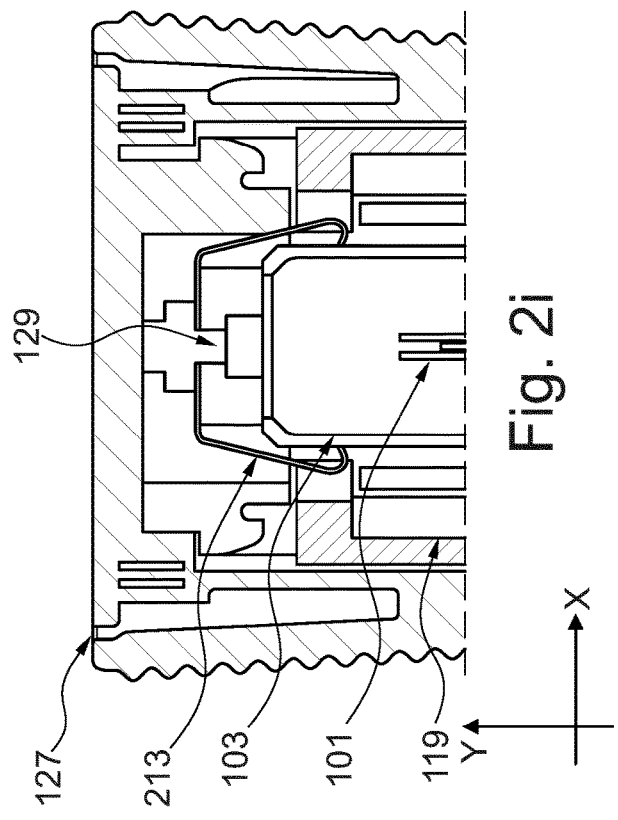

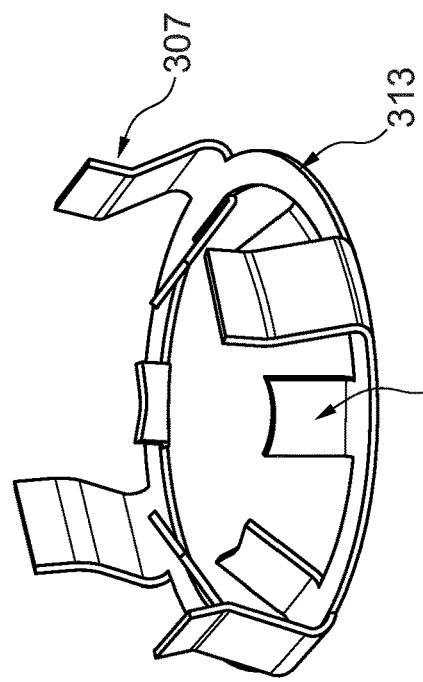
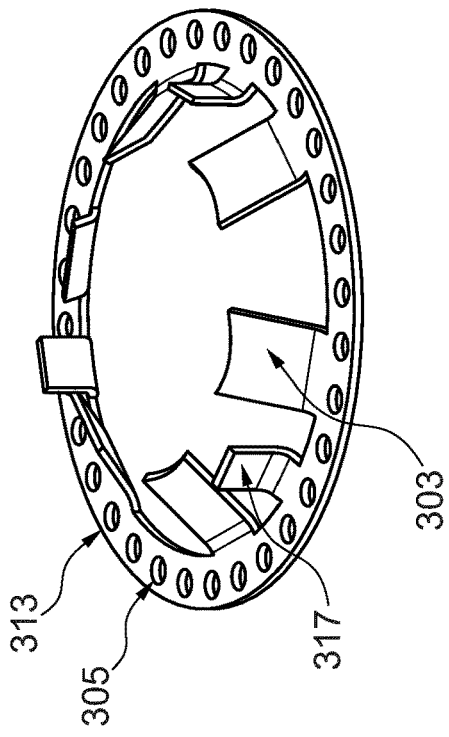
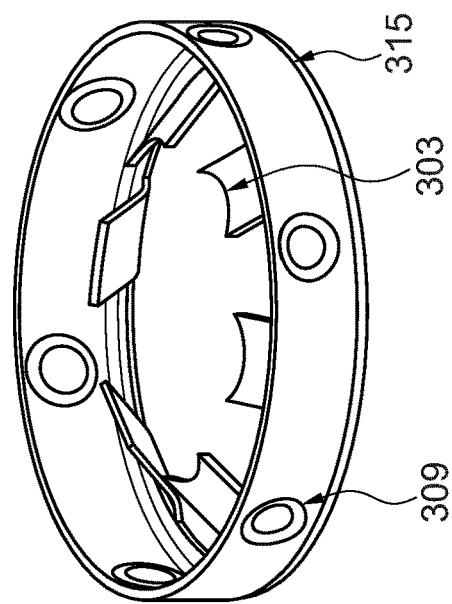
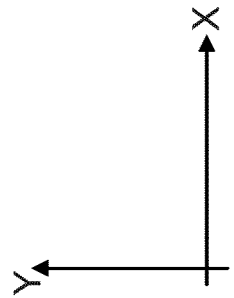

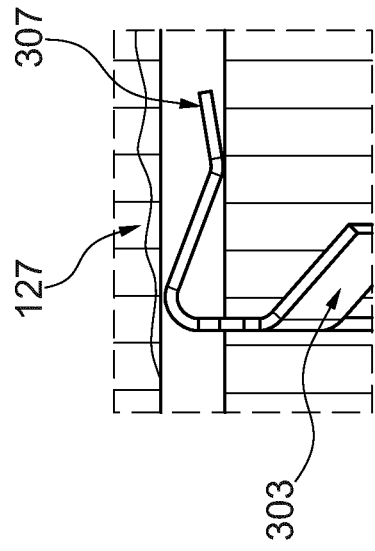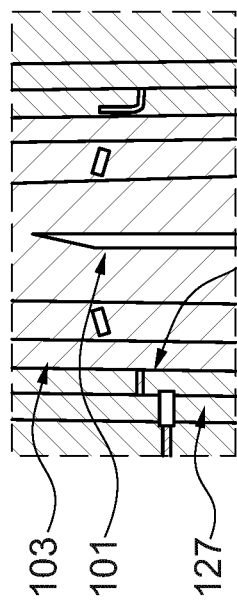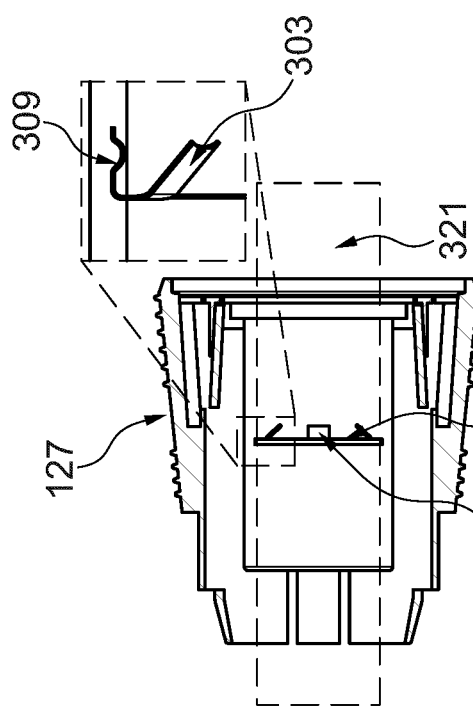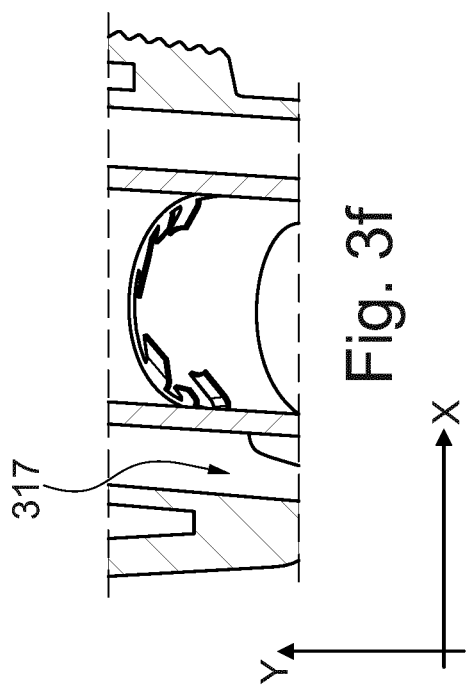

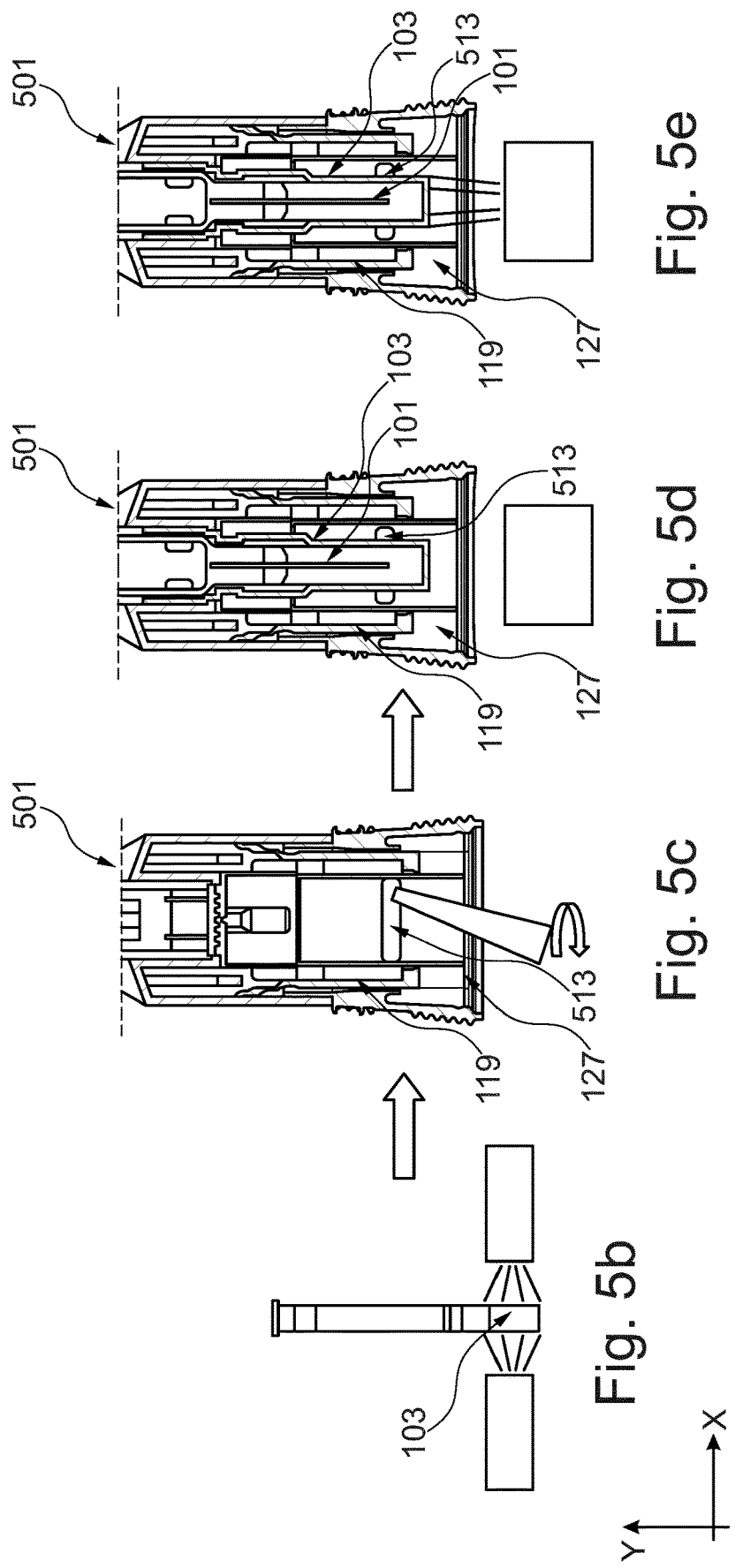

APPARATUS FOR REMOVING A NEEDLE SHIELD

CROSS REFERENCE TO RELATED APPLICATIONS

The present application is the national stage entry of International Patent Application No. PCT/EP2020/065364, filed on Jun. 3, 2020, and claims priority to Application No. EP 19305718.9, filed on Jun. 4, 2019, the disclosures of which are incorporated herein by reference.

TECHNICAL FIELD

The disclosure relates to apparatuses, for example apparatuses for removing a needle shield, and methods for manufacturing of the same as well as drug delivery devices.

BACKGROUND

Injection devices, such as auto-injectors, are known in the art for dispensing a medicament to the injection site of a patient. Such injection devices typically include a housing and a cap usually releasable connected to the housing. A syringe, usually including a needle, is sometimes located in the housing of the injection device (regularly prefilled with drug, i.e., a so-called pre-filled syringe), where the needle thereof is sometimes covered by a needle shield, which is removable. The needle shield may shield the interior of the syringe from the environment, e.g., to preserve long term sterility of the content of the reservoir. The cap may cover a distal end of the housing when attached to the housing. When the cap is detached, the syringe may be visible when closely inspecting the uncovered opening in the housing. For preparing the device for a delivery operation, cap and needle shield may have to be removed.

There are different types of needle shields, e.g., so called rigid needle shields (shortly named RNS) and soft needle shields (SNS). The interior of both types may be soft, whereas the types may differ in the outer surface or shell, which is rigid for the RNS and soft for the SNS. The RNS may be of multi-part construction (e.g., a rigid part receiving a soft part in its interior) and the SNS may consist of a single part, e.g., of an elastomeric material.

In order to prepare the device for delivering a dose, the protective needle shield has to be removed from the needle. This may be done by gripping or grabbing the protective needle shield and pulling it away from the needle.

There remains a need for improvements relating to the removal of the needle shield.

SUMMARY

Certain aspects provide an improved mechanism for removing the needle shield. These aspects are achieved by the methods, systems, and devices as disclosed herein, and the remaining disclosure may provide for advantageous embodiments and refinements.

In an aspect, an apparatus includes a needle unit including a needle arranged along a first axis, a needle shield which covers the needle, a main part, and a connector for connecting the needle shield to the main part by a positive connection or an adhesive bond, such that the needle shield is removed when the main part is moved along the first axis away from the needle.

One advantage of the proposed apparatus and all its variations is that the assembly is simple and the connector can be applied for different geometries and/or types of the needle shield. For example, the connector may be suitable for different needle shields which have different outer contours when looking onto the needle end of the syringe. One specific connector—for a positive or form-fit or for an adhesive connection—may advantageously be applied for a variety of needle shields of different shapes or types. Needle shields of the same type, e.g., RNSs or SNSs, may be available in a variety of geometries, e.g., including different regular and/or irregular outer contours. For example, the diameter may vary angularly, e.g., relative to the first axis along which the needle is oriented, and/or axially between different needle shields. The particular geometries of the RNS may vary from manufacturer to manufacturer, even for syringes nominally having the same volume of liquid in their interior. The connector may be designed to compensate the difference between different needle shields, be it in type or geometry. The needle may have an open end. The open end of the needle may form the needle outlet. A needle inlet—remote from the open end—may be arranged to be fluidly connected or may be fluidly connected with a liquid reservoir. Liquid may enter the needle through the inlet and leave the needle through the open end or outlet during operation of a drug delivery device. The reservoir may be a pre-filled syringe or a cartridge, for example.

In an exemplary embodiment the apparatus includes an attachment part wherein the attachment part is mechanically connected to the main part or wherein the attachment part is integrated into the main part. Attachment part and main part may establish or may form a unitary body structure. The attachment part may provide further options for connecting further parts to the main part, e.g., the connector, which are advantageous. Embodiments of these parts are described in the further embodiments. The attachment part may be axially offset from the needle away from the open end of the needle.

In a further exemplary embodiment the apparatus includes a cap. The cap may include the main part. The main part may provide an outer surface of the cap and/or define an inner space of the cap.

Thus, the needle shield may be arranged in the interior space and the cap may be connected to the needle shield space such that the needle shield is removed together with the cap, e.g., when the cap is detached from a housing of the device to which it was releasable attached.

In an embodiment, the cap includes a closing part which covers an opening of the main part remote from the needle or axially offset from the needle in a direction away from a needle opening. The closing part may be, e.g., permanently and/or non-releasably, connected to the main part, e.g., by a snap fit.

A multi-part cap with separate parts—e.g., the main part and at least one other part like the closing part—which are assembled together enables that the connector may be connected to the needle shield and/or to the main part or another part of the cap after the main part has been positioned relative to the needle shield in the intended position in which it should be connected to the main part, and in some embodiments the connector is connected to the cap before the closing part. The connector—for a positive connection or an adhesive bond—may be arranged in the main part and/or may be retained therein, either as a separate component or integrated into another part of the cap.

In an embodiment, at least a section of the connector or only a section of the connector is accessible through the opening, for example when the closing part is not connected to the main part or were removed from the main part, when it is connected.

In an embodiment, the connector may be not accessible when the closing part is connected to the main part. Therefore, once the closing part has been fitted to the main part, the connector may be shielded and no longer be accessible for manipulation due to the closing part preventing access to the connector. Accordingly, tampering with the connector is prevented by the closing part.

In a further exemplary embodiment the connector includes at least one arm or a plurality of arms. The (respective) arm may be movable. The (respective) arm may be deflectable, e.g., elastically and/or plastically, and/or deformable, e.g., elastically and/or plastically. The (respective) arm may extend along an outer surface of the needle shield. The outer surface may be a side surface which extends along the needle and/or originates from an end surface of the needle shield which covers the open end of the needle. The (respective) arm may be oriented along the first axis, e.g., parallel to the axis. The plurality of arms may define a retaining space in between the arms in which the needle shield is arranged. The (respective) arm may include at least one prong or barb. The prong or barb may be arranged close to a free end of the (respective) arm or form the free end. The prong or barb may extend radially inwards, e.g., from the (respective) arm and/or towards the needle shield, for example in order to establish a positive connection between the at least one prong or barb and the needle shield. The respective arm may be pivoting around or relative to a pivot. The pivot may be provided by and/or arranged in the main part. The pivot may be offset axially from the open end of the needle, e.g., away from the open end of the needle and away from the needle or remote from the needle inlet.

By means of the arm, the connection feature on the arm—e.g., the prong or barb—may be positioned at a desired position relative to the needle shield. As seen along the needle shield, the connection feature may be arranged axially at a location between the end of the needle shield and the open end of the needle.

In a further exemplary embodiment the apparatus includes a base part. The base part may extend obliquely, e.g., perpendicularly, to the first axis. The at least one movable arm may be connected to the base part.

The base part may be used to establish a connection between the connector and a further part, e.g., a part of the cap such as the main part or the closing part. Thus, the connector may be reliably secured relative to the main part and/or the closing part via the base part. The base part may be axially and/or rotationally secured with respect to the main part.

In an embodiment, the (respective) arm is radially supported against radial outward displacement and/or limited with respect to radial outward movement, e.g., by a support feature. The support feature may be arranged in the main part. The support feature may prevent disengagement of the connection feature and the needle shield, for example as radial outward movement is the direction away from the needle shield. The support feature may abut the arm or be arranged to abut the arm before the connection feature can disengage the needle shield. The support feature may be connected to, e.g., integral with, a part of the cap, e.g., the main part or the closing part. Alternatively, the support feature may be a separate part, e.g., a part which is movably retained in the housing to which the cap is connected. The support feature may be part of a needle cover. The needle cover may be arranged to cover the needle, for example after the cap has been removed and/or after the dispensing or injection operation has been performed with the device.

In a further exemplary embodiment the at least one movable arm originates from the base part, e.g., from a radial end-region of the base part, and extends along the first axis wherein the at least one movable arm in an end-region remote from the base part has a section which extends parallel or radially inwards towards the first axis. The inwardly extending section may be the connection feature of that arm, e.g., the prong or barb. The inwardly extending section may extend obliquely or perpendicularly to the first axis. The inwardly extending section may be oriented or directed rearward, e.g., towards the base part and/or extend along another section of the movable arm, which is, for example, radially outwardly offset from the inwardly extending section.

A reliably operating connector may be provided in this way. If the arm extends from a radial end region, manufacturing of the connector, e.g., by punching and bending, may be facilitated.

In a further exemplary embodiment the at least one movable arm penetrates or penetrates through the attachment part of the main part, for example directed towards the needle shield. In other words, the base part may be arranged on one side of the attachment part, e.g., a side facing away from the needle and/or the needle shield, and the arm(s) may extend towards the needle shield, e.g., through an opening defined by and/or laterally adjoining the attachment part. The arm(s) may extend to that side of the attachment part which faces the needle or the needle shield. The base part may be secured, e.g., positively connected and/or rotationally secured to the attachment part. The at least one movable arm may be positively connected via the prongs or barbs to the needle shield. The movable arms and the base part may be formed by a staple.

Assembling the apparatus in this embodiment is rather simple as it requires only the connector, e.g., a staple to positively connect the cap with the needle shield. Once the cap is removed also the needle shield will be removed. Furthermore, the required parts such as the cap, the separate connector, e.g., the staple, and the needle shield can be manufactured separately. For example, by using different staple sizes the apparatus for removing a needle shield can easily cope with different sizes and geometries of the needle shield. There is no need to adjust the geometries of the main part, the attachment part and/or the closing part. The connector can be guided axially such that the arm(s) travel along the outer surface of the needle shield without contacting the needle shield during the axial travel. Once the axial end position, e.g., a position where the base part abuts the attachment part, has been reached, the arms may be displaced inwardly. During this displacement, the arms may be plastically deformed—The connection feature on the arms may penetrate the needle shield, e.g., through the rigid outer shell, and establish the positive connection. Thus, the connector, e.g., a staple, can be located in the correct position without axial insertion forces acting on the needle shield. Only the prongs or barbs need to be pushed radially inwards, e.g., by an assembly tool, leading to a plastic deformation of the staple. This establishes a mechanical connection with the needle shield which enables the needle shield to be removed once the cap is removed. This embodiment requires no axial insertion force and has a reduced chance of interference with the container closure integrity (CCI), i.e., the tightness of a closure of a container such as a syringe which is closed by a needle shield.

In a further exemplary embodiment the base part is formed as a ground plate or base plate. The plate may have a connection feature for establishing a connection with the cap. The ground plate may have a breakthrough. The breakthrough may be the connection feature for establishing a connection with the attachment part. The breakthrough may be arranged at the first axis. The breakthrough may be provided for positively connecting or may positively connect the ground plate to the attachment part of the cap. The at least one movable arm which is connected to the ground plate, e.g., formed unitarily with the ground plate, may extend along the first axis and/or away from the ground plate such as towards the needle. The at least one movable arm may be directed away from the first axis, and includes at its end a barb which is bent towards the needle shield. The barb may be oriented towards the ground plate and/or extend along another section of the arm and/or between the arm and the needle shield. A plurality of arms may be circumferentially disposed and, for example, evenly distributed around the ground plate. The arm(s) may be elastically and/or plastically displaceable relative to the ground plate.

Also in this embodiment only few parts are required and it is comparatively simple to assemble. In contrast to the previous embodiment, where a plastically deformed staple may be employed, in this embodiment elastically and/or plastically deformable arms may employed. The arms may be directed away from the first axis. When the needle shield contacts the barbs, on account of their oblique orientation relative to the axis, the opening defined by the barbs may be widened, while the arms are elastically displaced. The elastic restoring force may maintain contact between the barbs and the needle shield. Alternatively, the opening defined by the arms may be configured to receive the needle shield without deforming or displacing the arms. In this case the opening may be dimensioned to receive the needle shield, e.g., there may be a circumferential gap between the needle shield and the barbs.

The connector of this embodiment enables to cope with different needle shield geometries or sizes as well, as the elastically and/or plastically deformable arms simply are bent radially further outward or inward to adapt to the shape and size of the needle shield. Once the ground plate is fixed to the attachment part the arms and/or the needle shield and the barbs have been properly positioned relative to one another, the barbs may be pushed towards the needle shield. The pushing may be effected by the closing part, e.g., by the movement for attaching the closing part to the main part. For example the support feature may force the arms inwardly against the needle shield to establish or strengthen the positive connection with the needle shield. The support feature may also support the arms radially outwardly against radially outward displacement. The support feature may be arranged inside the main part. This support feature can include a needle cover which is arranged along the first axis and movable along the first axis relative to the main part and/or relative to the needle. The support feature can also include a lid wedge or lid clip. This embodiment requires no insertion force, for example if the arms do not have to be deformed while they are guided along the needle shield and has a reduced chance of interference with the CCI.

In a further exemplary embodiment the closing part or the main part interacts with the support feature such that the arms are bent radially inwardly towards the needle shield. In this way a mechanical positive connection between the needle shield and the barbs is only established when the closing part is closing the main part which leads to a force directed radially inward from the support feature towards the arms and the barbs. For this embodiment no separate assembly tool is required to force the barbs into a positive connection with the needle shield. Also in this embodiment the assembly is simple and the main part, the connector and the needle shield can be manufactured separately. This embodiment not necessarily requires an insertion force—i.e., a force acting on the needle shield during insertion of the needs shield into a connector space laterally delimited by the connector, e.g., the arms—and has a reduced chance of interference with the CCI.

In a further exemplary embodiment the connector includes two movable arms which are arranged opposite to each other wherein the needle shield is arranged between the arms.

In a further exemplary embodiment the connector includes an annular disc or ring which surrounds the needle shield in order to establish a positive connection between the annular disc or ring and the needle shield. In this embodiment the connector may be limited axially to the needle shield, i.e., it does not extend axially beyond the needle shield. This embodiment may have advantages as the connection or mechanical interaction between the connector and the main part is effected laterally relative to the needle shield which may improve or facilitate the force transfer to the needle shield.

In a further exemplary embodiment the annular disc or the ring is embedded into the main part such that they cannot be separated non-destructively. This embedding can be achieved with a molding process as described below. The annular disc or the ring include barbs which are directed towards the needle shield so that a mechanical connection between the barbs and the needle shield is established. In this embodiment it is not required an additional assembly tool for establishing the positive connection between the barbs and the needle shield. The positive connection is established when the main part with the barbs covers the needle shield. The annular disc or the ring can and the barbs can include a metal and the main part can include a plastic which is molded around the annular disc or the ring. As a result using metal-barbs provide a stable and reliable connection between the barbs and the needle shield. Using plastic for the main part leads to lighter, lower cost device in total.

In a further exemplary embodiment the ring includes a circlip with a gap which allows the circlip to be elastically deformed so that the enclosed area can be increased or decreased, wherein the circlip has a smaller inner diameter than the needle shield so that the circlip applies a force to the needle shield when it surrounds the needle shield in order to establish a positive connection between the circlip and the needle shield. The circlip has also a positive connection with the main part. This embodiment provides a simple connector which can adapt to different sizes of needle shields due to its elastically deformable shape. Also it requires an assembly tool to adjust the circlip at the correct position but no insertion force.

In a further exemplary embodiment the adhesive bond is formed by an UV-curable adhesive. This embodiment requires even less mechanical parts and can also cope with different geometries of needle shields. It requires no insertion forces to establish an adhesive connection between the main part and the needle shield. This embodiment requires no insertion force and has a reduced chance of interference with the CCI.

In another aspect, a method for manufacturing an apparatus is provided including: providing a needle unit including a needle which defines a first axis, providing a needle shield, providing a main part, and forming a connector for positively connecting the needle shield with the main part, such that the needle shield can be removed when the main part or the cap with the main part is moved along the first axis away from the needle.

In an exemplary embodiment of the method the connector includes a ring which is co-molded directly into the main part for establishing a positive connection.

In a further exemplary embodiment of the method the connector includes an adhesive for establishing an adhesively bond with the needle shield to the main part, such that the needle shield is removed when the main part is moved along the first axis away from the needle.

In another aspect, a drug delivery device, for example an auto-injector, including the apparatus as disclosed herein is provided. The drug delivery device includes a housing, wherein the housing includes the cap with the closing part and wherein the housing covers the apparatus as described herein.

BRIEF DESCRIPTION OF THE FIGURES

Embodiments will now be described, by way of example only, with reference to the accompanying drawings, in which:

FIG. 1D is schematic cross-sectional drawing of a needle shield from one side;

FIG. 1E is a schematic cross-sectional drawing of a needle shield according to FIG. 1D, but turned by 90 degrees around a first axis;

FIG. 1F is a schematic cross-sectional drawing of an alternatively shaped needle shield;

FIG. 1G is a schematic cross-sectional drawing of a needle shield according to FIG. 1D with an assembly tool;

FIG. 1H is a schematic cross-sectional drawing of a needle shield as shown in FIG. 1G with a different position of the needle cover.

FIG. 1I is a schematic 3D-drawing of a top view of the main part with the mounted staple;

FIG. 2A is a schematic cross-sectional drawing of a second embodiment showing an excerpt of a cap, a needle shield and the connector;

FIG. 2B is a schematic cross-sectional drawing similar to FIG. 2A, but the cap and the connector moved towards the needle;

FIG. 2C is a schematic 3D-drawing of the connector;

FIG. 2D is a schematic 3D-drawing of the lid of the cap;

FIG. 2E is a schematic 3D-drawing of an excerpt of the main part and the connector;

FIG. 2F is a schematic 3D-drawing showing the connector being connected to the attachment part of the main part from a side view;

FIGS. 2G-2J are schematic cross-sectional drawings of the main part and the connector being attached to a cap clip and of the assembly of the lid of the cap providing the radial force to the connector;

FIG. 3A is a schematic 3D-drawing of a third embodiment showing an annular disc with tabs and barbs;

FIG. 3B is a schematic 3D-drawing of a modified third embodiment showing a ring with arms and barbs;

FIG. 3C is a schematic 3D-drawing of a modified third embodiment showing a ring with indents and barbs;

FIG. 3D is a schematic cross-sectional drawing of the main part, the ring with barbs and an insert from a side view;

FIG. 3E is a schematic cross-sectional drawing of an excerpt similar to the magnified part of FIG. 3D. Instead of indents here flexible arms of the ring are molded into a side wall of the main part;

FIG. 3F is a schematic cross-sectional drawing of an excerpt of a main part with a ring;

FIG. 3G is a schematic cross-sectional drawing of an excerpt of the needle shield;

FIG. 5B is a schematic cross-sectional drawing of the plasma treatment of a needle shield;

FIGS. 5C-5E are schematic cross-sectional drawings of the drug delivery device and the steps for applying an adhesive for connecting the needle shield to the main part.

DETAILED DESCRIPTION

The same reference numbers apply to the same features.

Figure 1A:
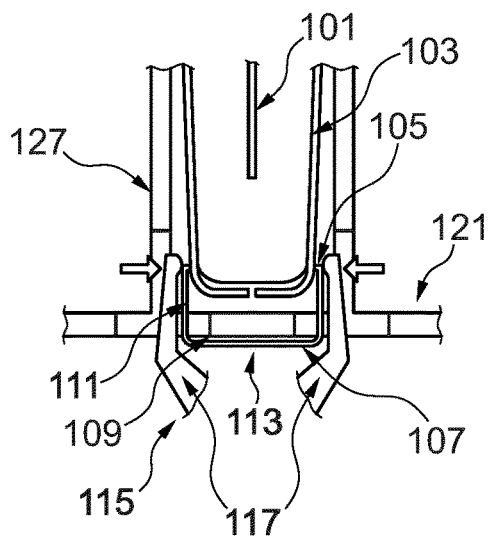
FIG. 1A is a schematic cross-sectional view of a first embodiment showing a staple connected with a cap and a needle shield.

FIG. 1A is a schematic cross-sectional view of a first embodiment. It shows an excerpt of a cap 121, a needle shield 103, a needle 101 and a connector 113, 213, 313, 315, 413, 513 including a staple 113. The needle 101 is arranged along a first axis Y, surrounded by the needle shield 103. The cap 121 includes a main part 127 which covers the needle shield 103 and further includes an attachment part 109 which is disposed across the main part 127. The main part 127 can also be named as cap tube 127.

The staple 113 includes a base part 107 which extends perpendicular to the first axis Y. It includes arms 111 extending along the first axis Y away from the base part 107 and towards the needle 101, wherein the base part 107 connects the arms 111. At the arms 111 prongs 105 are disposed which extend radially inwards towards the needle shield for establishing a positive connection.

The staple 113 is arranged such that the arms 111 penetrate through the attachment part 109 of the cap 121 in the direction of the needle shield 103 along the first axis Y. The attachment part 109 is arranged between the base part 107 and the prongs 105 on the first axis Y, thereby connecting the staple 113 with the cap 121 and the needle shield 103.

FIG. 1A further shows an assembly tool 115 for adjusting the staple 113 with respect to the needle shield 103. The assembly tool 115 includes lever arms 117 which are used to apply a force at the endings of the arms 111 of the staple 113 directed radially inward, so that the prongs 105 are squeezed into the needle shield 103.

It is further shown a schematic coordinate system with a first axis Y and a second axis X, which is arranged at a right angle to the first axis Y accordingly wherein both the first- and the second axis Y and X are arranged at the drawing level.

Figure 1B:
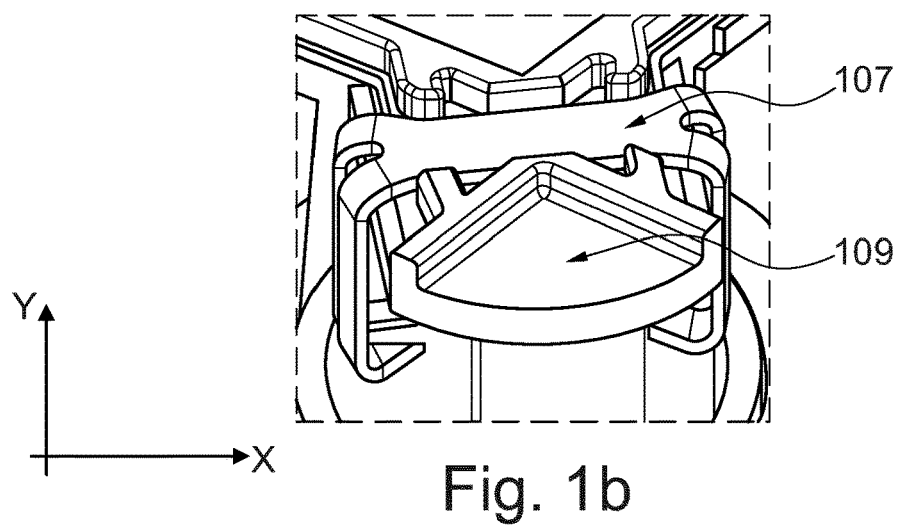
FIG. 1B is a schematic 3D-drawing, showing an excerpt of the attachment part and the staple.

FIG. 1B is a schematic 3D-drawing, showing an excerpt of the attachment part 109 of the cap 121 and the staple 113. The base part 107 of the staple 113 is arranged across the attachment part 109 and the arms 111 of the staple 113 are elongated along the first axis with the prongs 105 at their endings radially directed inwards to the needle shield 103 (not shown in this figure). The base part 107 and the attachment part 109 establish a positive connection such that the base part 107 and subsequently the staple 113 is radially secured.

Figure 1C:
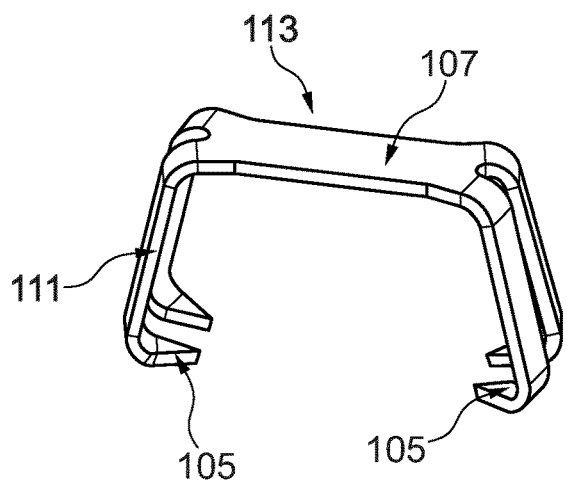
FIG. 1C is a schematic 3D-drawing of the staple.

FIG. 1C is a schematic 3D-drawing of the staple 113 including a base plate 107, four arms 111 and a prong 105 at each ending of each arm 111. The arms 111 are connected by the base plate 105 forming a U-shape. The prongs 105 are directed radially inwards towards the needle shield 103 and the first axis Y. The arms 111 are arranged in pairs facing each other on opposite sides of the first axis Y. It is also possible that the arms 111 are arranged with another distance, such as equal distance, between each other in the radial direction around the first axis Y wherein the distance of the arms 111 to the first axis Y is always the same. It is also possible that the staple 113 includes two, three or more than four arms 111. Instead of prongs 103 the arms 111 can also include barbs 203 or other sharp or pointed endings which can grab the needle shield 103. Barbs 203 in contrast to prongs 103 have an ending with a larger angular extension, e.g. with a plurality of points.

FIG. 1D is schematic cross-sectional drawing of the apparatus which is 180 degrees turned around the second axis X with respect to FIG. 1A. It shows the main part 127 and a needle cover 119. The staple 113 is connected to the needle shield 103 having a cross-sectional plane which crosses the first axis Y wherein the width of the needle shield 103 is larger than the depth of the needle shield 103. The depth of the needle shield extends into a direction perpendicular to the drawing plane. The cross-section of the needle shield 103 is shown from a first side with its width which extends perpendicular to the first axis Y and parallel to the second axis X. The base part 103 of the staple 113 is such that the arms 111 closely cover the width of the needle shield 103.

FIG. 1E is a schematic cross-sectional drawing of an excerpt of the main part 127 of FIG. 1D in a cross-sectional view from a second side which is turned by 90 degrees around the first axis Y with respect to the view of FIG. 1E. The cross-section of the needle shield 103 is shown from a second side with its depth which extends in this view also parallel to the second axis X. The base part 103 of the staple 113 is such that between the arms 111 and the needle shield 103 is some space. The staple 113 is connected to the needle shield 103 across the depth of the needle shield 103, which can be also named grip flats. The arms 111 of the staple 113 cover the width of the needle shield 103 with a remaining space between the needle shield 103 and the arms 111 of the staple 113 which is similar on both sides of the needle shield 103. Such needle shields 103 are for example used in pre-filled syringes available from Becton Dickinson.

FIG. 1F is a schematic cross-sectional drawing of an excerpt of the main part 127 in a cross-sectional view wherein the needle shield 103 has an alternative shape compared to FIG. 1D and 1E. In this view the largest diameter across the needle shield 103 is shown. The needle shield 103 has flattened edges. The cross-section of this needle shield 103 according to this embodiment can be circular. Such needle shields 103 are used in pre-filled syringes available from Ompi.

FIG. 1G is a schematic cross-sectional drawing of a similar cross-sectional view compared to FIG. 1D. Additionally in FIG. 1G are shown the lever arms 117 of the assembly tool 115 for adjusting the staple 113 at the needle shield 103. The lever arms 117 apply a force to the endings of the arms 111 of the staple 113 directed radially inward, so that the prongs 105 are squeezed into the needle shield 103. The assembly tool 115 can move in the direction of the first axis Y and so requires less radial clear space in the main part 127.

FIG. 1H is a schematic cross-sectional drawing of a similar cross-sectional view compared to FIG. 1G. In FIG. 1H the needle cover 119 is at a lower position with respect to the first axis Y. It is also possible that adjusting the staple 113 could potentially happen in the same step as the priming step with the needle cover 119 pushed further down (e.g., more than 3 mm, such as 3.13 mm) increasing the radial space available for the assembly tool. The priming process enables the drug delivery device 501 such as an auto-injector 501 to be used by a user. During the priming process the needle cover 119 is moved in the direction of the needle 101.

FIG. 1I is a schematic 3D-drawing, showing an excerpt of the attachment part 109 of the main part 127 and the staple 113 from the top. Further it is shown the needle cover 119.

The advantage of this embodiment and its variations is that the assembly is very simple, the parts, i.e., needle shield 103, main part 127 and staple 113 can be manufactured separately. From FIGS. 1D and 1E it can be seen that the staple 113 can be adapted to different geometries of the needle shield 103. Finally it requires no axial insertion force and has a reduced chance of interference with the container closure integrity (CCI). Complicated structures for locating the staples such as location bosses can be avoided.

Figure 2L:
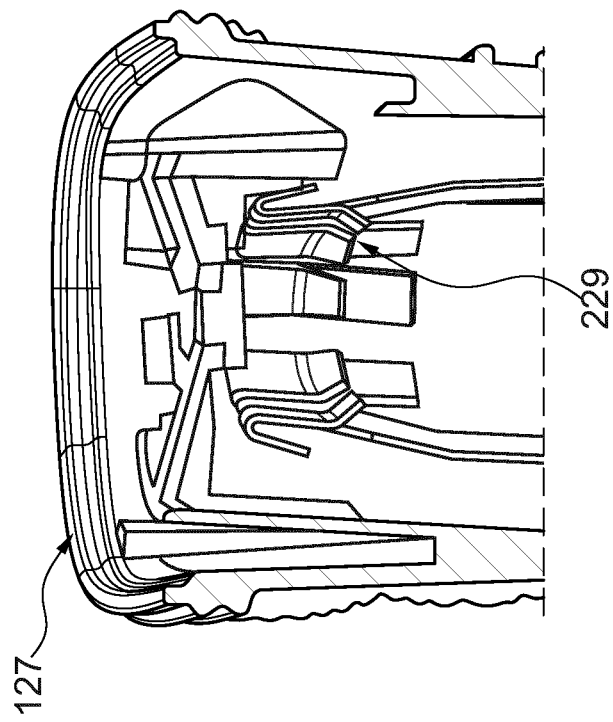
FIG. 2l is a schematic 3D-drawing of a cross-section of the main part.

FIG. 2A is a schematic cross-sectional drawing of a second embodiment. It shows an excerpt of the cap 121 with the attachment part 109 and the main part 127, a needle shield 103, a needle 101 and the connector 213 which includes a ground plate 201 and arms 205 which are attached to the ground plate 201. The arms 205 extend along the first axis Y, away from the ground plate 205 and towards the needle 101. The arms 205 are directed away from the first axis Y in the direction of the second axis X and subsequently open up an angle between the arms 205 and the first axis Y. The arms 205 include at their endings barbs 203 which are bent towards the needle shield 103. Because the arms 205 are directed away from the first axis Y the arms 205 together with the barbs 203 can cover and connect a needle shield 103 which has a greater cross-section than the diameter of the ground plate 201 of the connector 213. In order to have a strong connection between the barbs 203 and the needle shield 103, e.g., when the cap 121 together with the connector 213 is moved away from the needle 101, the angle between the bent barbs 203 and arms 205 is 90 degrees or smaller than 90 degrees. The connector 213 and the arms 205 with the barbs 203 can include plastic or metal.

FIG. 2B is a schematic cross-sectional drawing similar to FIG. 2A, but including the closing part 123 including a lid 123 of the cap 121 which has moved towards the needle shield 103 in the direction of the first axis Y engaging barbs 203 of the connector 213 along with the arms 205 so that the barbs 203 are connected to the needle shield 103.

FIG. 2C is a schematic 3D-drawing of the connector 213. The connector 213 includes a ground plate 201 with a breakthrough 207 which can be in the center of the ground plate 201. The breakthrough 207 can have various shapes such as rectangular, squared, circular, or any other shape for mechanically fixing the ground plate 201 to the attachment part 109 of the main part 127.

FIG. 2D is a schematic 3D-drawing of the closing part 123 which can be lid 123 of the cap 121. Lid blocks 125 of the lid 123 force the barbs 203 of the connector 213 towards the needle shield 103 when the lid 123 is attached to the main part 127.

FIG. 2E is a schematic 3D-drawing of an excerpt of the main part 127 with the attachment part 109 and the connector 213 below the attachment part 109. It further shows the needle cover 119.

FIG. 2F is a schematic 3D-drawing of the connector 213 being connected to a cap clip 129 which is part of the attachment part 109 of the main part 127 from a side view. The connector 213 is mechanically connected to the cap clip 129 via the breakthrough 207 of the base plate 201.

FIGS. 2G-2J are schematic cross-sectional drawings of the main part 127 and the connector 213 being attached to the cap clip 129 and the needle shield 103. In this embodiment the connector 213 can include a metal.

FIGS. 2G and 2H are schematic cross-sectional drawings where the connector 213 is initially assembled to the main part 127. The connector 213 is clear of both the needle cover 119 and needle shield 103 when they are assembled. FIG. 2G shows a turned view of 90 degrees around the first axis Y with respect to the view of FIG. 2H.

FIGS. 2I and 2J are schematic cross-sectional drawings where the lid 123 of the cap 121 is assembled to the main part 127. It forces the metal barbs 203 to bend inwards towards the needle shield 103 and make contact with the needle shield 103. The barbs 203 are designed to contact sufficiently the needle shield 103 in the lower diameter section as shown in FIG. 2J, and the barbs 203 will flex and have a stronger contact with the needle shield 103 across its larger diameter, shown in FIG. 2I.

The advantage of this embodiment and its variations is that the assembly is very simple, only few parts are required and it requires no or only little insertion force and has a reduced chance of interference with the CCI.

Figure 2K:
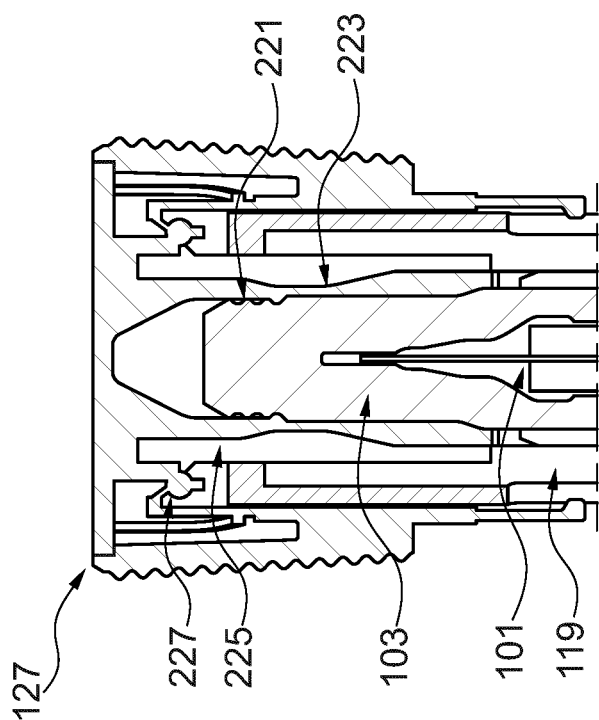
FIG. 2K is a schematic cross-sectional drawing of the main part with support features.

FIG. 2K is a schematic cross-sectional drawing of the main part 127. It shows a needle 101, a needle shield 103 and a needle cover 119. Along the needle shield 103 in the direction of the first axis Y lid wedges 221 are placed and next to them in the direction radially outward from the needle 101 slope guides are positioned. Further the assembly includes a clip 225 which locks the lid wedges 221 into place. The slope 223 guides the needle shield 103 into a central position with respect to the first axis Y. It further includes optionally a lid clip 227. If the lid 123 of the cap 121 is moved downwards along the first axis Y the lid wedges 221 are moved radially inward towards the needle shield 103 such that a press fit connection emerges. This essentially relies on the insertion force of the lid 123 being much greater than the cap removal force which is in the order of 35N.

FIG. 2I is a schematic cross-sectional drawing of the main part 127. At the main part 127 elastically deformable beams 229 which can be include prongs 105 or barbs 203 are arranged radially. Those beams 229 are able to cope with a variety of geometries of the needle shield 103. They typically include plastic and are molded in one step with the cap 121 or the main part 127 as is also described in FIGS. 3D-3G. The variation of the geometries of the needle shield 103 could cover a radial difference between the needle shield 103 between the lower and higher diameter section, which has a diameter of 0.5 mm. It is also possible to use various beam 229 geometries for adjusting to the different geometries and sizes of the needle shield 103. As an increased elastically deformability of the beams 229 leads to decreased stiffness of the beams and therefore less force which can be applied to the needle shield 103 a balance between elastically deformability and applicable force needs to be found. As an example if for the removal force 35N are required and the coefficient of friction is 0.2 6 clips are required which contact the RNS with a force of 29N per clip. With a beam 229 length of 6 mm, a width of 4 mm and a depth of 2 mm it would require 0.3 mmm deflection to this contact force to a diameter of a needle shield 103 of Becton Dickinson and would plastically deform if there is an additional deflection of 0.5 mm. One could consider elastic solutions with only plastic parts, for example, where the variability of the RNS is accounted for by wedging plastic parts.

FIG. 3A is a schematic 3D-drawing of a third embodiment showing an annular disc 313 with holes 305. The annular disc 313 includes an inner- and an outer radius. Between the inner- and outer radius the holes 305 are arranged at the annular area. The annular disc 313 further includes barbs 303 and tabs 317 which are disposed at the inner radius of the annular disc 313. The tabs 317 are for locating an insert 321 which is used for the process of co-molding of the annular disc 313 with the main part 127 as described in FIGS. 3D and 3E. The barbs 303 are for grabbing the needle shield 103. The annular disc 313 includes 6 barbs 303 which are disposed equally spaced around the inner side of the annular disc 313. The number of barbs 303 can also be less or more than six.

FIG. 3B is a schematic 3D-drawing of a modified third embodiment showing an annular disc 313 without holes 305 but with flexible arms 307 which include a wrinkle and which are mounted on the outer radius of the annular disc 313. The flexible arms 307 are used for the molding process described in FIG. 3D. The annular disc 313 further includes barbs 303 which are disposed at the inner radius of the annular disc 313 as described in FIG. 3A.

FIG. 3C is a schematic 3D-drawing of a modified third embodiment showing a ring 315 with indents 309 and barbs 303. The ring 315 includes a shallow body wherein the barbs 303 are arranged in a circular manner at the inside of the ring 315. The barbs 303 and the inner wall of the ring 315 form an angle smaller than 90 degrees. The ring 315 includes 6 barbs 303 which are disposed equally spaced around the inner side of the ring 315. The number of barbs 303 can also be less or more than six.

FIG. 3D is a schematic cross-sectional drawing of the setup for co-molding the annular disc 313 or ring 315 with the main part 127. In order to co-mold the annular disc 313 or ring 315, which can include metal, with the main part 127, the annular disc 313 or ring 315 first needs to be mounted onto an injection molding tool. The inner core of the molding tool includes a two part insert 321. For this co-molding process the annular disc 313 or ring 315 are placed into a mold (not shown) where the main part 127 is formed around the annular disc 313 or ring 315 with a commonly known injection procedure using for example plastic as forming material. The two part insert 321 holds the annular disc 313 or ring 315 at its defined location in relation to the main part 127 and additionally fills up the empty space in the main part 127 so that the injected fluid plastic flows around the insert 321, forming the main part 127 and encloses the annular disc 313 or ring 315. Once the plastic is firm again the annular disc 313 or ring 315 and the main part 127 are co-molded such that the annular disc 313 or ring 315 and the main part 127 cannot be separated non-destructively. By use of the indents 309 the bond between the ring 315 and the main part 127 can be additionally strengthened. Other alternative methods for holding the annular disc 313 or ring 315 on the molding tool are tabs 303 or flexible arms 307, see FIGS. 3A-C.

Additionally a small part of the schematic drawing is magnified and marked with a dashed square. In this magnified part indents 309 of the ring 315 are shown by which the ring 315 is molded into a side wall of the main part 127. Thereby the liquid plastic can flow into and around the ring 315 and the indents 309.

The same applies if not the ring 315 but an annular disc 313 is co-molded with the cap 121. Here, the liquid plastic flows around the annular disc 313 and through the holes 305 or the flexible arms 307.

FIG. 3E is a schematic cross-sectional drawing of an excerpt similar to the magnified part of FIG. 3D. Instead of indents 309 here flexible arms 307 of the ring 315 are molded into the main part 217. Thereby the part of the main part 127 where the ring 315 is fixed includes liquid plastic so that the plastic can flow into and around the ring 315 and the indents 309 and the ring 315 and the main part 127 are finally co-molded as described in FIG. 3D.

FIG. 3F is a schematic cross-sectional drawing of an excerpt of a main part 127 in a cross-sectional view. It shows a section of the ring 315 with some barbs 303 which are directed upwardly with respect to the first axis Y, away from the needle 101. At the same lateral position as the ring 315 is positioned also tabs 317 are positioned for locating the insert 321 into the mold.

FIG. 3G is a schematic cross-sectional drawing of and excerpt of the needle shield 103, indicating that approximately 0.5 mm radial clearance of the ring 315 with the RNS. It also might be ensured that the location features are clear.

Figure 3J:
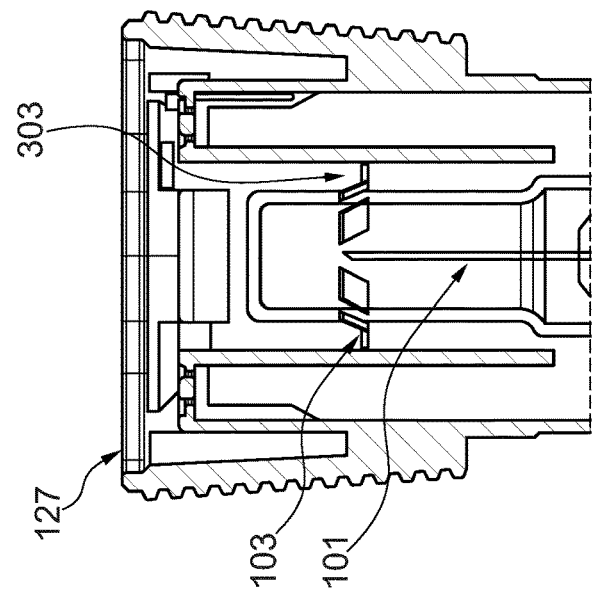
FIG. 3J is an excerpt of a different needle shield than those in FIGS. 3H and 3I in a cross-sectional view, showing the interaction of the barbs with the needle shield.
Figure 3I:
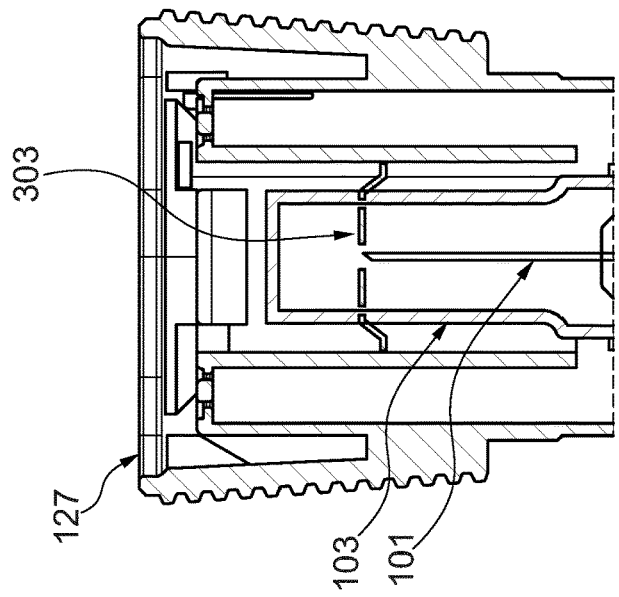
FIG. 3I is a schematic cross-sectional drawing of an excerpt of the needle shield of FIG. 3H in a cross-sectional view from a second side, showing the interaction of the barbs with the needle shield.
Figure 3H:
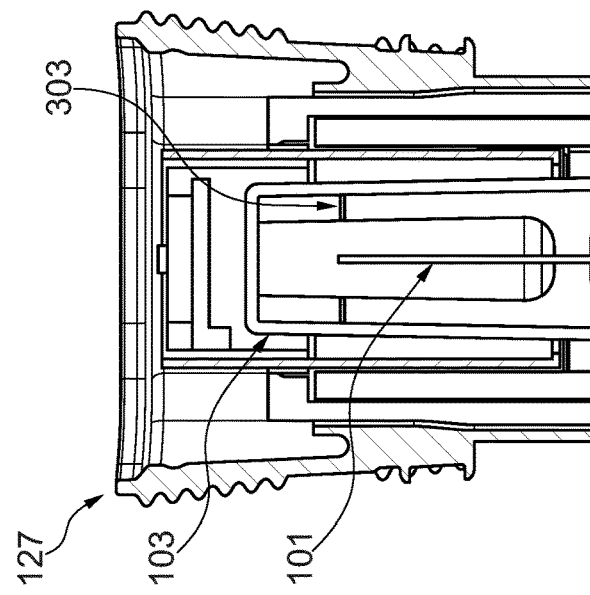
FIG. 3H is a schematic cross-sectional drawing of an excerpt of a needle shield in a cross-sectional view from a first side, showing the interaction of the barbs with the needle shield.

FIG. 3H is a schematic cross-sectional drawing of an excerpt of the main part 127 with a needle shield 103 in a cross-sectional view from a first side. The needle shield 103 having a cross-sectional plane which crosses the first axis Y wherein the width of the needle shield 103 is larger than the depth of the needle shield 103. The cross-section of the needle shield 103 is shown from a first side with its width which extends parallel to the second axis X. It shows further the needle 101, the needle shield 103 and the barbs 303 of the annular disc 313 or ring 315 interacting with the needle shield 103.

FIG. 3I is a schematic cross-sectional drawing of an excerpt of the main part 127 with a needle shield 103 in a cross-sectional view from a second side, which is turned by 90 degrees around the first axis Y with respect to FIG. 3H. It also shows the barbs 303 of the annular disc 313 or ring 315 interacting with the needle shield 103. In this view it is shown the cross-section of the depth of the needle shield 103. Such needle shields are used in pre-filled syringes available from Becton Dickinson.

FIG. 3J is a schematic cross-sectional drawing of an excerpt of a different needle shield 103 than those shown in FIGS. 3H and 3I in a cross-sectional view. In this view the largest diameter across the needle shield 103 is shown. It also shows the barbs 303 of the annular disc 313 or ring 315 interacting with the needle shield 103. Such needle shields are used in pre-filled syringes available from Ompi.

The advantage of this embodiment and its variations is that the part of the connector is very simple, the assembly of the apparatus is also simple and it can handle a tolerance of the location of the connector 213.

Figure 4A:
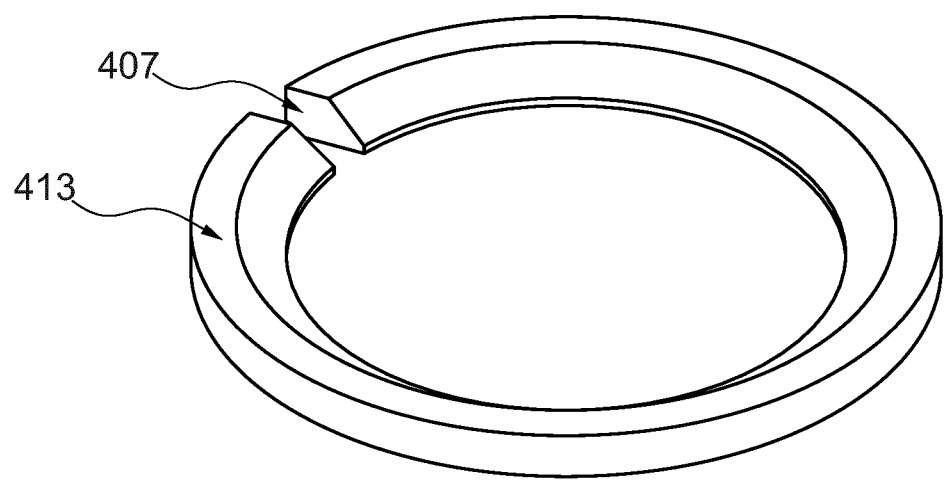
FIG. 4A is a schematic 3D-drawing of a fourth embodiment showing a circlip.

FIG. 4A is a schematic 3D-drawing of a fourth embodiment showing a circlip 413 with a gap 407 such that the circlip is not closed. The gap 407 allows to bend the circlip so that the gap 407 is increased and the area which is enclosed by the circlip 413 is increased. In the same manner the circlip 413 can be bent so that the gap 407 decreases and subsequently the area which is enclosed by the circlip 413 is decreased. The bent is an elastic deformation so that without applying a force to keep the bent the circlip will return to its original form and the original gap size. The circlip 413 has an inner- and outer radius and a certain thickness. From the outer radius towards the inner radius the circlip 413 includes a slope indicating a cone-form towards the inner radius.

Figure 4B:
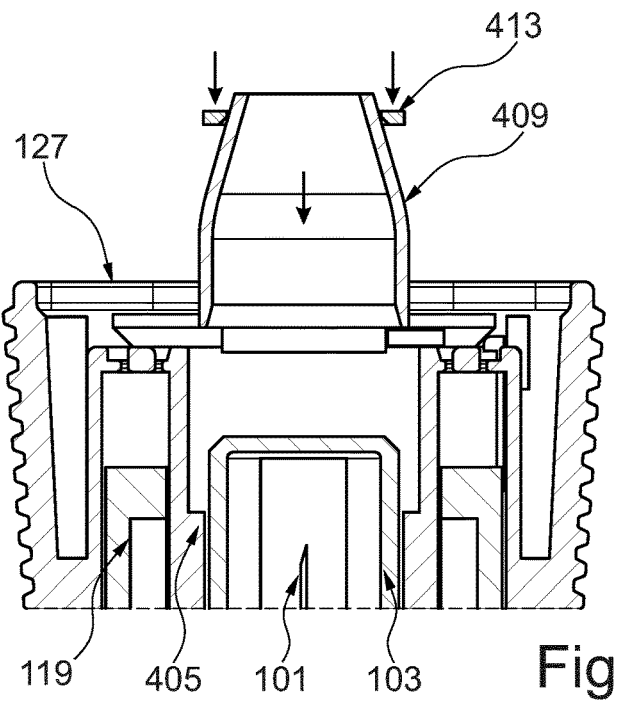
FIG. 4B-4D are schematic cross-sectional drawings of the assembly process when the circlip is being attached to the main part.

FIG. 4B is a schematic cross-sectional drawing of an excerpt of the main part 127 in a cross-sectional view including an assembly tool 409, also named as taper tool 409 for the circlip 413 which will be mounted onto the lip 405. It is further shown the needle 101, the needle shield 103 and the needle cover 119. In the assembly process the circlip 407 is stretched out radially over the assembly tool 409 which has a larger diameter than the circlip 407. In the next step the assembly tool 409 with the circlip 407 is then pushed downwards in the direction of the needle 101 along the first axis Y.

Figure 4C:
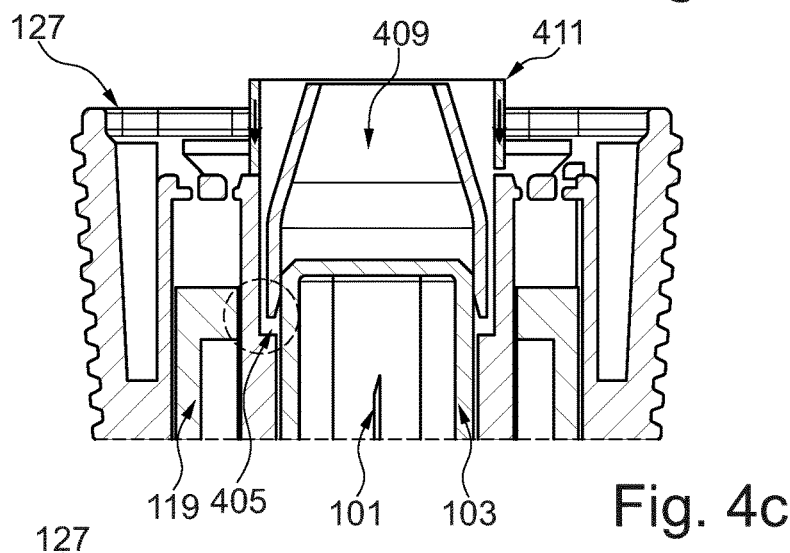

FIG. 4C is a schematic cross-sectional drawing of the final position of the assembly tool 409 when it is stopped at the lip 405. In this position the circlip 413 is pushed off the end of the assembly tool 409 by a plunger tool 411.

Figure 4D:
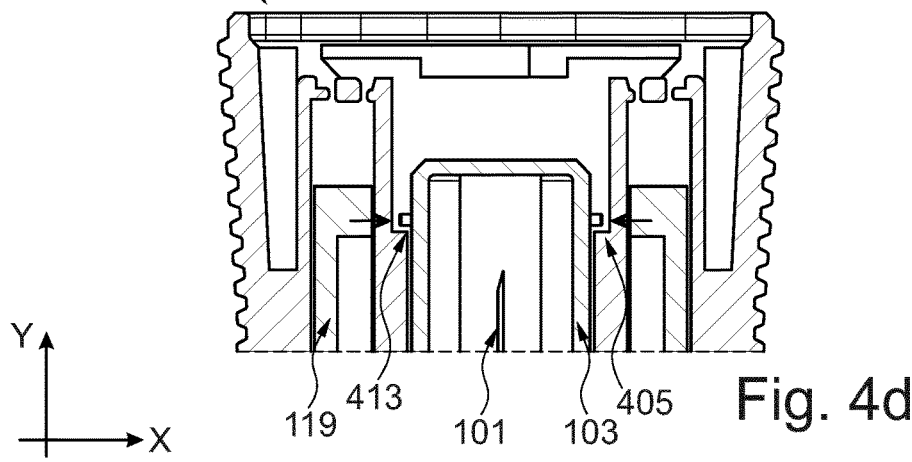

FIG. 4D is a schematic cross-sectional drawing of an excerpt of the main part 127 in a cross-sectional view including a lip 405 on which the circlip 413 rests in the final mounted position around the needle shield 103. The lip 405 also serves to couple the circlip 413 to the main part 127 or the cap 101 so that the circlip 413 and needle shield 103 are removed when the main part 127 or the cap 101 is removed. It is also shown the needle cover 119 and the needle 101.

The advantage of this embodiment and its variations is that the assembly is very simple, the parts, i.e., needle shield 103, main part 127 and circlip 413 can be manufactured separately. The circlip 413 can be adapted to different geometries of the needle shield 103. Finally it requires no insertion force and has a reduced chance of interference with the CCI.

Figure 5A:
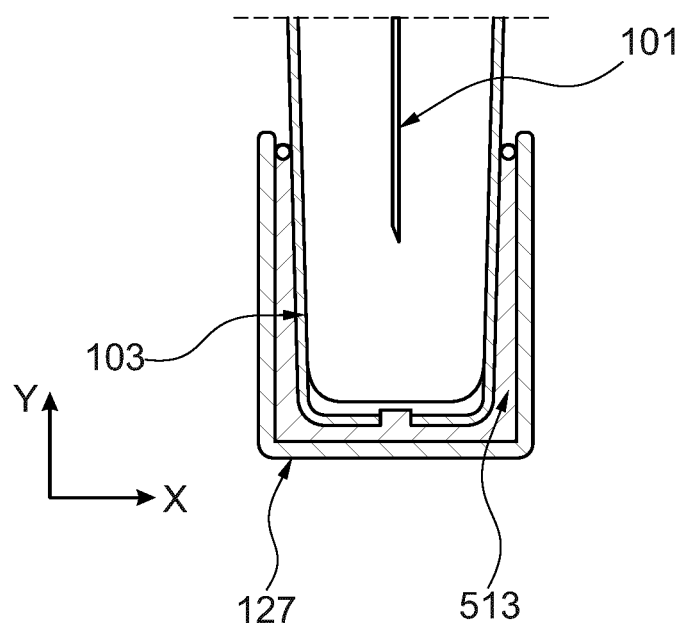
FIG. 5A is a schematic cross-sectional drawing of a fifth embodiment showing the needle shield being adhesively connected to the main part.

FIG. 5A is a schematic cross-sectional view of a fifth embodiment showing the needle shield 103 being adhesively connected with an adhesive 513 to the main part 127. It further shows a needle 101.

In some embodiments, an UV cure adhesive is used as it is advantageous when the device is immediately after assembly being refrigerated. It is required that the adhesive 513 will be fully cured before refrigeration. The main part 127 needs to be designed such that an access for the dispensation of the adhesive is possible.

This UV-cure can be applied for example to an acrylic like Loctite 3926 which is rather viscous. Once the correct wavelength and light intensity is set the UV-cure is very fast and can be finished within seconds. Also an inline inspection regarding the presence of an adhesive is possible as it fluoresces when it is exposed to black light.

FIGS. 5B-5E describe the steps for applying an adhesive for connecting the needle shield 103 with the main part 127.

FIG. 5B is a schematic cross-sectional drawing of the needle shield 103 being plasma treated. It includes a millisecond application of high heat to increase the surface energy. By this plasma treatment the needle shield 103 (polypropylene) the bond strength will greatly increase.

FIG. 5C is a schematic cross-sectional drawing of excerpt of a drug delivery device 501 wherein the adhesive 513 is dispensed in a ring around the main part 127 through a hole at the lid 123 of the main part 127.

FIG. 5D is a schematic cross-sectional drawing of a schematic excerpt of a drug delivery device 501 wherein a pre-filled syringe is assembled into the main part 127.

FIG. 5E is a schematic cross-sectional drawing of a schematic excerpt of a drug delivery device 501 wherein UV light is applied within a few seconds of dispensing to fully cure adhesive 513. The duration of the UV-light application depends on depth but is generally less than 30 s.

The advantage of this embodiment and its variations is that the assembly is very simple, with no separate connector component required. The amount of adhesive applied can be adapted to suit different geometries of the needle shield 103. Finally it requires no insertion force and has a reduced chance of interference with the CCI.

The connector for establishing a positive- or an adhesive bond and all described embodiments can be applied to a RNS as well as to a SNS. A RNS includes a rigid outer surface but with a less rigid material (soft) at the inner side of the needle shield. A SNS includes less rigid material (soft) throughout the shield. The force for removing needle shields can be 20N or higher, e.g., 25N or higher or 30N or higher.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis Y of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis Y of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29)

human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(w-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

LIST OF REFERENCES

101 Needle
103 Needle Shield
105 Prongs
107 Base part
109 Attachment part
111 Arms 113 Staple
115 Assembly tool
117 Lever arms
119 Needle Cover
121 Cap
123 Closing part
125 Lid blocks
127 Main part
129 Cap clip
201 Ground plate
203 Barbs
205 Arms
207 Breakthrough
213 Connector
221 Lid wedges
223 Slope
225 Clip
227 Lid clip
229 Beams
303 Barbs
305 Holes
307 Flexible arms
309 Indents
313 Annular disc
315 Ring
317 Tabs
405 Lip
407 Gap
409 Assembly tool
411 Plunger tool
413 Circlip
501 Drug delivery device
513 Adhesive

The invention claimed is:

1. An apparatus, comprising:
   a needle unit comprising a needle arranged along a first axis;
   a needle shield which covers the needle;
   a main part; and
   a connector for connecting the needle shield to the main part by a positive connection or an adhesive bond, such that the needle shield is removed when the main part is moved along the first axis away from the needle,
   wherein the connector comprises at least one movable arm which extends along an outer surface of the needle shield,
   wherein the at least one movable arm penetrates through an attachment part of the main part directed towards the needle shield, and
   wherein a free end of the at least one moveable arm axially overlaps with the needle shield along the first axis.

2. The apparatus according to claim 1, wherein the attachment part is mechanically connected to the main part or the attachment part is integrated into the main part such that the main part and the attachment part form a unitary body structure.

3. The apparatus according to claim 1, further comprising:
   a cap comprising the main part, wherein the main part provides an outer surface of the cap and defines an inner space of the cap; and
   a closing part which covers an opening of the main part remote from the needle, wherein at least a section of the connector is accessible through the opening when the closing part is not connected to the main part, and wherein the connector is not accessible when the closing part is connected to the main part.

4. The apparatus according to claim 1, wherein the at least one movable arm comprises at least one prong or barb which extends radially inward towards the needle shield in order to establish a positive connection between the at least one prong or barb and the needle shield.

5. The apparatus according to claim 1, comprising a base part which extends perpendicular to the first axis and wherein the at least one movable arm is connected to the base part.

6. The apparatus according to claim 5, wherein the at least one movable arm originates from a radial end-region of the base part and extends along the first axis, and wherein the at least one movable arm in an end-region remote from the base part has a section which extends parallel or radially inwards towards the first axis.

7. The apparatus according to claim 5, wherein the base part is positively connected and/or rotationally secured to the attachment part and the at least one movable arm is positively connected via at least one prong or barb to the needle shield.

8. The apparatus according to claim 5, wherein the base part is formed as a ground plate with a breakthrough arranged at the first axis for positively connecting the ground plate to the attachment part of the main part, and wherein the at least one movable arm which is connected to the ground plate extends along the first axis away from the ground plate and towards the needle, wherein the at least one movable arm is directed away from the first axis, and wherein the at least one movable arm at its end comprises a barb which is bent towards the needle shield.

9. The apparatus according to claim 1, wherein the at least one movable arm is supported against radially outward displacement by a support feature arranged inside the main part.

10. The apparatus according to claim 1, wherein the at least one movable arm comprises two movable arms which are arranged opposite to each other, and wherein the needle shield is arranged between the two movable arms.

11. The apparatus according to claim 1, wherein the connector comprises an annular disc or ring which surrounds the needle shield in order to establish a positive connection between the annular disc or ring and the needle shield.

12. An auto-injector comprising an apparatus according to claim 1, and a housing, wherein the main part is connected to the housing and the needle is retained in the housing.

13. A method for manufacturing an apparatus, wherein the method comprises:
   providing a needle unit comprising a needle which defines a first axis;
   providing a needle shield;
   providing a main part; and
   forming a connector for positively connecting the needle shield with the main part, such that the needle shield can be removed when the main part or a cap with the main part is moved along the first axis away from the needle,
   wherein the connector comprises at least one movable arm which extends along an outer surface of the needle shield,
   wherein the at least one movable arm penetrates through an attachment part of the main part directed towards the needle shield, and
   wherein a free end of the at least one moveable arm axially overlaps with the needle shield along the first axis.

14. An apparatus comprising
a needle unit comprising a needle arranged along a first axis,
a needle shield,
a main part that covers the needle shield, and
a connector for connecting the needle shield to the main part by a positive connection or an adhesive bond, such that the needle shield is removed when the main part is moved along the first axis away from the needle,
wherein the connector comprises at least one movable arm which extends along an outer surface of the needle shield,
wherein the at least one movable arm penetrates through an attachment part of the main part directed towards the needle shield, and
wherein a base part extends perpendicular to the first axis and the at least one movable arm is connected to the base part, and the base part is arranged on one side of the attachment part facing away from the needle shield.

* * * * *